(12) United States Patent
Baussant (10) Patent No.: US 10,732,318 B2
(45) Date of Patent: Aug. 4, 2020

(54) BIOSENSOR DEVICE, SYSTEM AND METHOD FOR MONITORING A DEEP-WATER SEA-FLOOR

(71) Applicant: NORCE Norwegian Research Centre AS, Bergen (NO)

(72) Inventor: Thierry Baussant, Stavanger (NO)

(73) Assignee: NORCE Norwegian Research Centre A, Bergen (NO)

( * ) Notice: Subject to any disclaimer, the term of this patent is extended or adjusted under 35 U.S.C. 154(b) by 550 days.

(21) Appl. No.: 15/506,783

(22) PCT Filed: Aug. 21, 2015

(86) PCT No.: PCT/EP2015/069256
§ 371 (c)(1),
(2) Date: Feb. 27, 2017

(87) PCT Pub. No.: WO2016/030297
PCT Pub. Date: Mar. 3, 2016

(65) Prior Publication Data
US 2017/0276829 A1 Sep. 28, 2017

(30) Foreign Application Priority Data

Aug. 25, 2014 (SE) ...................................... 1450988

(51) Int. Cl.
*G01V 8/10* (2006.01)
*G01N 33/18* (2006.01)
(Continued)

(52) U.S. Cl.
CPC ............. *G01V 8/10* (2013.01); *G01N 33/186* (2013.01); *G01V 1/38* (2013.01); *E21C 50/00* (2013.01); *G01V 11/002* (2013.01)

(58) Field of Classification Search
CPC ............................... G01N 33/186; G01V 1/38
See application file for complete search history.

(56) References Cited

U.S. PATENT DOCUMENTS

2011/0227731 A1* 9/2011 Iffergan .................. F41H 11/05
340/541

OTHER PUBLICATIONS

Shaish et al.; "Fixed and suspended coral nurseries in the Philippines: Establishing the first step in the "gardening concept" of reef restoration", Journal of Experimental Marine Biology and Ecology, Amsterdam, NL, vol. 358, No. 1, Mar. 7, 2008, pp. 86-97.

(Continued)

*Primary Examiner* — Edward Park
(74) *Attorney, Agent, or Firm* — Renner, Otto, Boisselle & Sklar, LLP (57) ABSTRACT

A biosensor device (10) for in situ monitoring of deep-water sea-floor biological patterns (30), which biosensor platform (10) comprises a plurality of cameras (12) and a lightening system (14), wherein a plurality of coral nubbins (16) with a plurality of polyps (18) are prepared and fixed to a platform (11) of the biosensor platform (10) with a distance to each other such that there is no overlap on a picture frame (22) thereof, and wherein the cameras (12) and the lightening system (14) are arranged so as to take coral-silhouette-pictures (CSP:s) of the plurality of nubbins (16) in the picture frame (22). In this way, there is provided a biosensor device based on coral, or other deep-sea species, behavioural for surveillance and monitoring of a deep-water sea-floor.

14 Claims, 5 Drawing Sheets

(51) Int. Cl.
*G01V 1/38* (2006.01)
*E21C 50/00* (2006.01)
*G01V 11/00* (2006.01)

(56) References Cited

OTHER PUBLICATIONS

Suzuki et al.; "Development of underwater monitoring wireless sensor network to support coral reef observation", International Journal of Distributed Sensor Networks 2014, Taylor and Francis Inc., USA, vol. 2014, Apr. 19, 2014, pp. 1-5.
Roberts et al.; "A new laboratory method for monitoring deep-water coral polyp behavior", Hydrobiologia Mar. 1, 2002 Kluwer Academic Publishers, NL, vol. 471, Mar. 1, 2002, pp. 143-148.
Shafir et al.; "The use of coral nubbins in coral reef ecotoxicology testing", Biomolecular Engineering, Elsevier, NY, USA, vol. 20, No. 4-6, Jul. 1, 2003, pp. 401-406.
Fabricius-Dyg et al.; "Imaging of surface $O_2$ dynamics in corals with magnetic micro optode particles", Marine Biology (2012) 159, pp. 1621-1631.

\* cited by examiner

BIOSENSOR DEVICE, SYSTEM AND METHOD FOR MONITORING A DEEP-WATER SEA-FLOOR

This application is a national phase of International Application No. PCT/EP2015/069256 filed Aug. 21, 2015 and published in the English language, which claims priority to Swedish Patent Application No. 1450988-9 filed Aug. 25, 2014, which are hereby incorporated herein by reference in their entirety.

TECHNICAL FIELD

The present disclosure relates generally to the field of biosensors and more particularly to biosensors for monitoring biological patterns on a deep-water sea-floor.

BACKGROUND

Because of requirements on Oil and Gas (O & G) operators, typically from environmental authorities to monitor environmental impacts during Oil and Gas (O & G) drilling activities in sensitive environments such as a deep-water sea-floor with corals, there is a need to monitor coral status and impact on this environment, especially during such activities. Guidelines have been prepared to mitigate the environmental risk of drilling activities in areas with coral populations (Den Norske Veritas, DNV, 2012). In areas where drilling activities are close to coral populations, such as areas with coral reefs, the O&G operators typically have to apply costly mitigation actions to protect the corals. This often leads to applying a precautionary principle as there is no current technology known to document impact and monitor coral, or other deep-sea species, status during drilling activities.

Until now, according to our best understanding, there are no known techniques to measure effect on coral status or other deep-sea species continuously. Current techniques to assess impact of drill cutting plumes used by O&G operators are based on current measurements, turbidity measurements, sediment traps, sediment samples and visual mapping, all techniques typically not being continuously.

References describing known techniques and background are listed under the heading "list of references" in this disclosure.

Regarding monitoring such as visual mapping, for instance, the Guidelines (DNV, 2012) states that in general it is difficult to find an appropriate parameter for monitoring directly of corals, which will reflect any influences from drilling activities. High resolution still photos have from experience not been able to identify change in polyp behaviour on corals such as Lophelia pertusa when exposed to drill cutting sedimentations such as drill cutting plumes.

In particular, none of the known techniques are providing an actual measurement of the impact or changes of coral end-points from drill cutting sedimentations, but are only proxy measurements of drill cutting potential exposure, not their effect.

SUMMARY

According to one illustrative embodiment, the present invention is related to a biosensor device for in situ monitoring of deep-water sea-floor biological patterns. The biosensor device comprises a plurality of cameras and a lightening system. A plurality of coral nubbins with a plurality of polyps are prepared and fixed to a biosensor platform of the biosensor device with a distance to each other, of the coral nubbins, such that there is no overlap on a picture frame thereof. The cameras and the lightening system are arranged so as to take coral-silhouette-pictures of the plurality of nubbins in the picture frame.

Herein, the term "biological pattern" includes, without limitation, corals and other species.

According to another illustrative embodiment, the present invention is related to a system for in situ monitoring of deep-water sea-floor biological patterns. The system comprises at least one bio sensor device according to the above described embodiment.

The biosensor device comprises or is connected to an analytical system for in situ processing of coral data based on the coral-silhouette-pictures.

In this way, there is provided a biosensor device based on coral, or other deep-sea species, behavioural for surveillance and monitoring of a deep-water sea-floor, in particular for monitoring biological patterns on a deep-water sea-floor.

According to another illustrative embodiment, the present invention is related to a method for monitoring deep-water sea-floor biological patterns with a biosensor platform comprising a plurality of cameras and a lightening system. A plurality of coral nubbins with a plurality of polyps are prepared and fixed to the biosensor platform with a distance to each other such that there is no overlap on a picture frame thereof. The cameras and the lightening system are arranged so as to take coral-silhouette-pictures of a plurality of nubbins in the picture frame. The method further comprises taking coral-silhouette-pictures followed by measuring the coral silhouettes of each coral nubbin in an analytical system, typically including an expert analytical unit, for in situ processing of coral data including at least the coral silhouette.

In this way, a device system and method are provided that achieve monitoring and measuring biological patterns, in particular coral polyp activity, continuously and assess changes related to environmental parameters. This has not been disclosed until now.

BRIEF DESCRIPTION OF DRAWING FIGURES

The foregoing and other features of the present disclosure will become more fully apparent from the following description and appended claims, taken in conjunction with the accompanying drawings. Understanding that these drawings depict only several embodiments in accordance with the disclosure and are; therefore, not to be considered limiting of its scope, the disclosure will be described with additional specificity and detail through use of the accompanying drawings.

FIG. 1a is a schematic sectional view of a biosensor device in accordance with an illustrative embodiment on a deep sea-floor in the vicinity of a coral reef, and FIG. 1b, an enlargement of part of the biosensor device 10 shown in FIG. 1a;

DETAILED DESCRIPTION OF EMBODIMENTS

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

According to an aspect of the disclosure, a time-lapse camera system was used to continuously record pictures of corals nubbins having coral polyps placed on the biosensor platform of the biosensor device as described above in a deep-water sea-like environment. Studies showed that polyp activity of coral nubbins is changing relatively fast due to changes from their environment and that drill cuttings sedimentation affect their behavior. This may have important consequences for the coral physiological state as deep-sea corals are completely dependent on catching organic particles from their environment which they do by extending their tiny tentacles when food is available. Experiments showed that coral polyp activity may either increase or decrease significantly during and following an exposure to drill cutting sedimentation reflecting a disruption in their ability to catch prey.

Figures 1A, 1B:
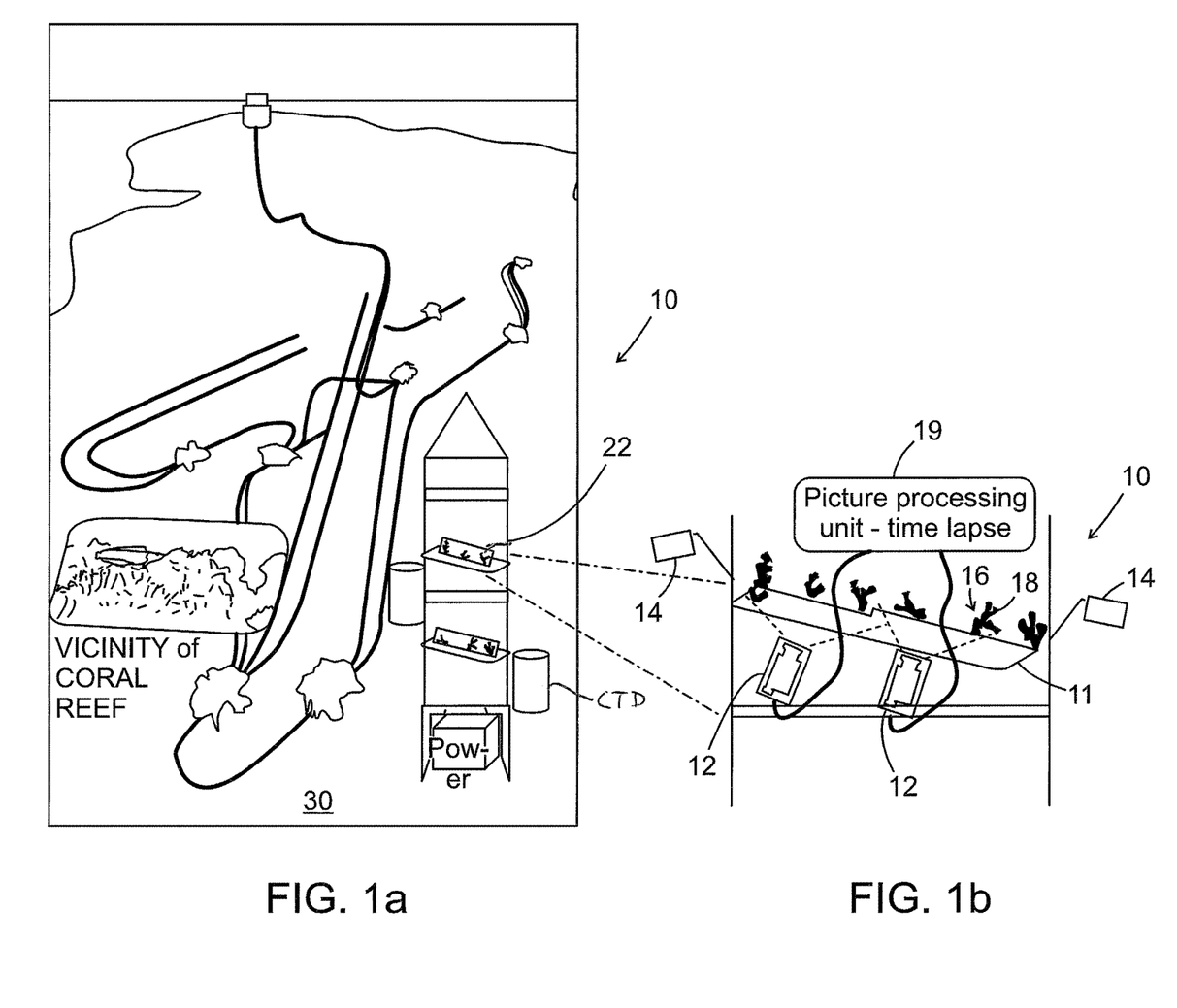

Referring to FIG. 1a, a schematic sectional view of a biosensor device 10 in accordance with an illustrative embodiment is shown on a deep-sea sea-floor 30 and to FIG. 1b, an enlargement of part (biosensor platform) of the biosensor device 10 is shown.

According to an embodiment, the present disclosure is directed to a biosensor device 10 for in situ monitoring of deep-water sea-floor biological patterns, typically in real-time. The biosensor device 10 comprises a plurality of cameras 12, typically high resolution (HD) cameras, and a lightening system 14. A plurality of coral nubbins 16 with a plurality of polyps 18 are prepared and fixed to a biosensor platform 11 of the biosensor device 10 with a distance to each other such that there is no overlap on a picture frame 22 (see FIG. 1a) thereof. The bio sensor platform 11 can be a grid or any other surface onto which coral nubbins 16 can be placed and live. Typically, the coral nubbins 16 comprise 4 to 8 polyps 18 and have a tree-like structure, but also other structures are possible depending on environment. As shown in FIG. 1a, there can be more than one platform 11, for instance two as shown, but any number of platforms 11 is possible, including also one only. According to an embodiment, the biosensor device comprises nubbins from deep-sea corals positioned "adequately" (See FIG. 1b) on the platform 11 of the biosensor device 10 which may be part of a conventional rig, such as a benthic rig structure, for deep-sea measurements and having low-power low light sensitive underwater HD cameras to measure and analyse coral polyp behaviour in real-time, typically in vicinity of corals, such as a coral reef. Herein the term "adequately" means that the coral nubbins 16 with a plurality of polyps 18 are prepared and fixed to a biosensor platform 11 of the biosensor device 10 with a distance to each other such that there is no overlap on a picture frame 22. Also conventional sensors such as sensors for measuring turbidity, CTD may be provided on the biosensor device 10. Since these are well known for the skilled-person they are not described in more detail.

As shown in FIG. 1b, which is an enlargement of part of the biosensor device 10, one of the platforms 10, the cameras 12 and the lightening system 14 are arranged so as to take coral-silhouette-pictures of the plurality of, or at least several, nubbins in the picture frame. In FIG. 1b two lightening systems 14 are shown only as an illustrative example. The number of cameras 12 will typically depend on space available, power requirements and number of coral nubbins.

Typically, the biosensor device 10 comprises coral nubbins from a deep-sea coral such as Lophelia pertusa positioned adequately on the platform of the biosensor device 10, such as a rig, and underwater HD-cameras that measure and analyse coral polyp activity in real-time. However, without departing from the disclosure, also other herein not explicitly stated biological patterns can be monitored.

The biosensor device 10 may also comprise a picture processing unit 19 for time-lapse picture shooting, and in situ processing, typically pre-processing, of the pictures taken to measure the whole coral nubbin silhouette, typically an area thereof, which will change over time. These changes, for instance of the coral silhouette area, will reflect the activity of the polyps in relation to their environment over time, which will be described in more detail as follows. The processing unit 19 may also be used for communication with a system for processing coral and/or picture data, including an expert analytical unit, which will be described below with reference to FIG. 2.

Figure 2:
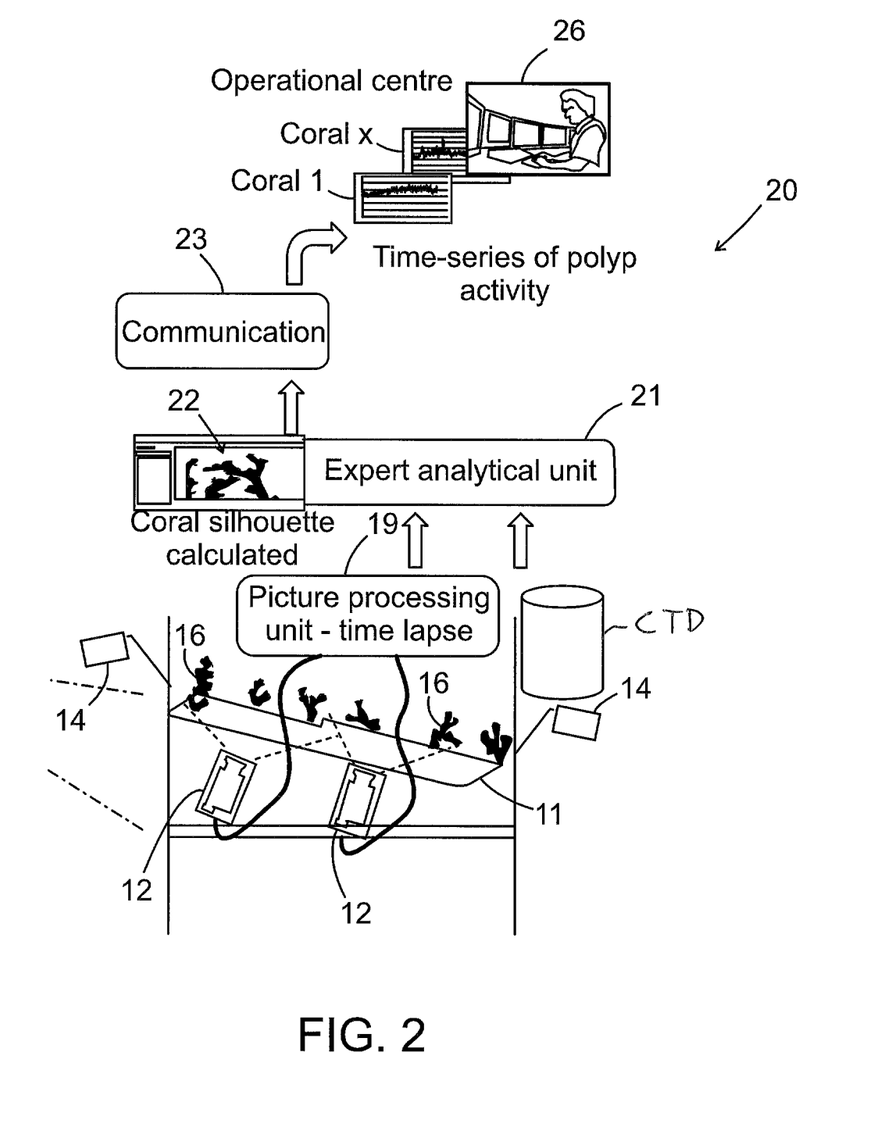
FIG. 2 is a schematic view of a system comprising at least one biosensor device as illustrated in FIG. 1a-b in accordance with an illustrative embodiment.
Figure 3:
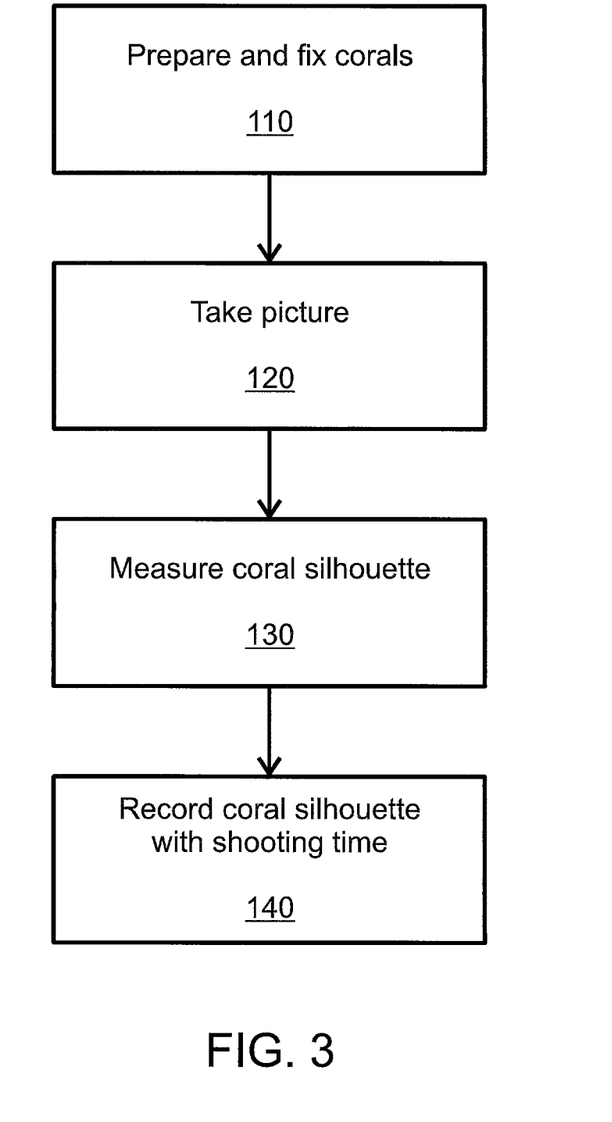
FIG. 3 is a flow-chart of a method according to an embodiment.

Now is also referred to FIG. 2, which shows a schematic view of a system for monitoring deep-sea-floor biological patterns and to FIG. 3, which is a flow-chart of a method for monitoring deep-sea-floor biological patterns according to an embodiment of the disclosure.

According to an embodiment, in a biosensor system 20 for monitoring deep-water sea-floor biological patterns more than one biosensor device 10 may be provided. Typically, offshore, the biosensor devices 10 are deployed on the sea-floor at a natural site for a coral reef (See FIG. 1a) and at a distance between 300 and 500 meters or any other distance considered safe by regulation for instance.

According to an embodiment, the biosensor system 20 further comprises an analytical system, typically an expert analytical unit, 21 for in situ processing of coral data received from the biosensor device(s) 10. The analytical unit 21 may also transmit other data, such as control data to the biosensor device 10. The biosensor system 20 may also further comprise a communications unit 23 adapted to transmit coral data including at least measured coral silhouette CS data, to an operational centre 26 that can communicate with the biosensor system 20. The system 20 may be partly or wholly provided separately from the biosensor device 10, typically over sea.

According to an embodiment, the analytical system, including the expert analytical unit, 21 is arranged to give each coral nubbin 16 a unique identification ID, and the coral silhouette picture CSP and its coral silhouette area CSA thereof is arranged to be recorded automatically with shooting time. This is schematically shown in FIG. 2, in that data for a first coral, Coral 1 is separated from data for another coral, Coral X.

Figure 4:
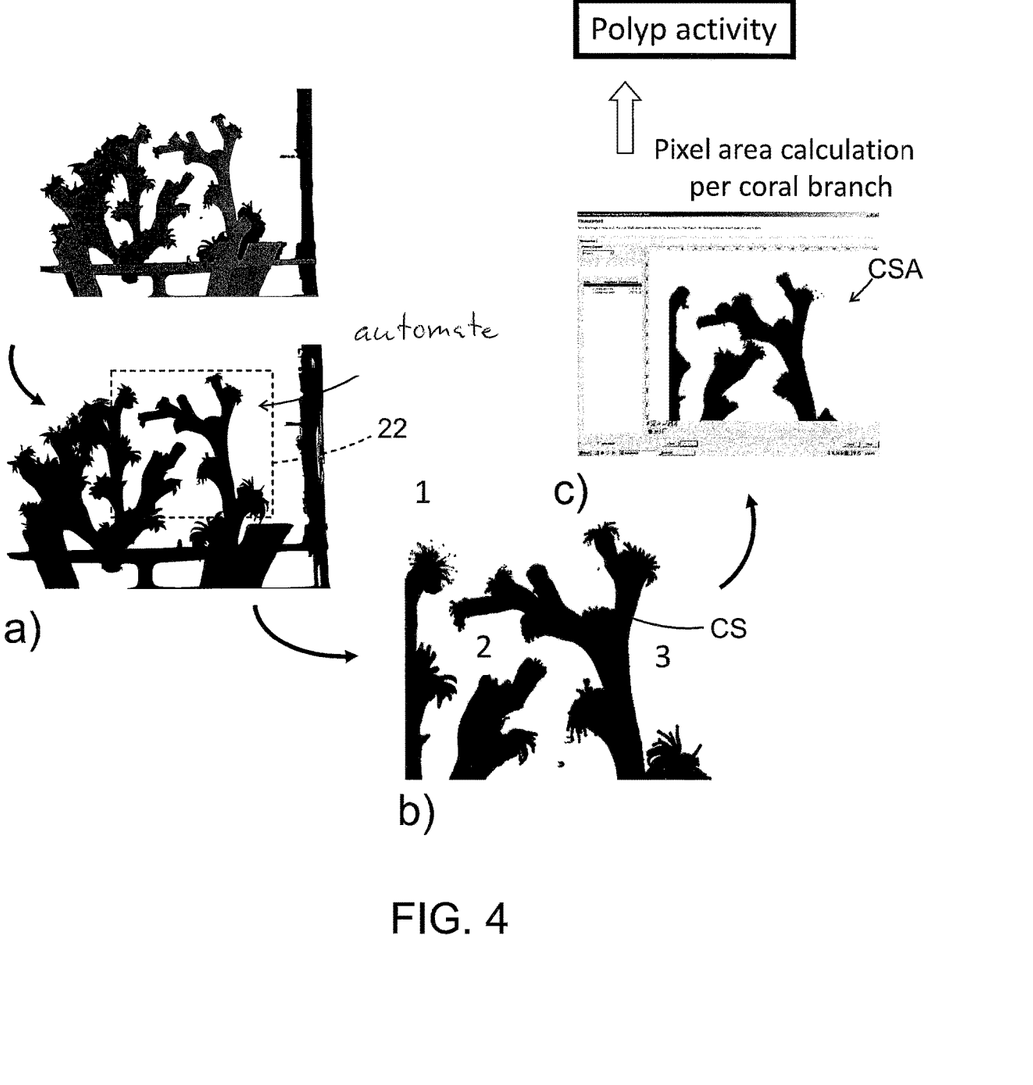
FIG. 4a is a view of a picture window (frame) taken from the corals on the platform.
FIG. 4b is an enlargement of the picture window and FIG. 4c shows pixel area calculation per coral branch.

Now is also referred to FIG. 4a is a view of a picture window taken from the corals on the platform, FIG. 4b is an enlargement of the picture window and FIG. 4c shows pixel area calculation per coral branch.

Typically, the lightening system 14 and the cameras 12 are adapted to be turned on during a period of time of 1 to 5 minutes so as to reduce power consumption and coral light-exposure. When operating, the biosensor device 10 including the lightening system 14 will be kept most of the time in the dark, which is normal for corals at this depth, and to reduce power consumption, lightening will be turned on only during shorter periods (say 2 minutes) to take (shoot) 120 a picture 22 (See FIG. 3) for measurement. Typically, a principle of the measurement will be based on regular time-lapsed picture shooting, acquisition and in situ processing of the picture 22 to measure the whole coral nubbin silhouette, in short "coral silhouette", CS. For each picture 22, the coral silhouette CS will be measured, typically calculated in the analytic system 21 after pre-processing of the picture in the processing unit 19.

As an example, corals are collected from a clean site and maintained in a laboratory under field conditions for acclimation. Inshore, coral nubbins 16 with 4 to 8 polyps are prepared and fixed 110 on the biosensor device 10 on the platform 11. The shape of the coral nubbins 16 are typically "tree-like" (dichotomy) and each nubbin is placed at a distance allowing no overlap on the picture frame 22.

Changes of the coral silhouette CS over time T can be measured 130 by the calculation of a silhouette perimeter or total coral silhouette area CSA, for instance by pixel area calculation per coral branch. These changes will reflect the activity of the coral polyps in relation to their environment over time. The shooting will depend on the power requirement and the picture processing capacity. Each coral nubbin will be given an ID and the coral silhouette measurement recorded automatically in an excel format file with shooting time. The file can be transmitted to a shore station or the operational centre 26 of an O&G rig, and the data downloaded by end-users where they can be visualized. The data from contextual sensors like turbidity, added to the rig, will also be processed by the rig expert analytical unit 21 and accessible by end-users at the operational centre 26. The changes of coral polyp activity will be related to environmental event and on-going industrial activities. Critical decisions relative to industrial discharge and operations will be made depending on the effect observed.

Now is referred to FIG. 5a-b, which show time-lapse-video-on/off experiment during 1 month time.

Figure 5:
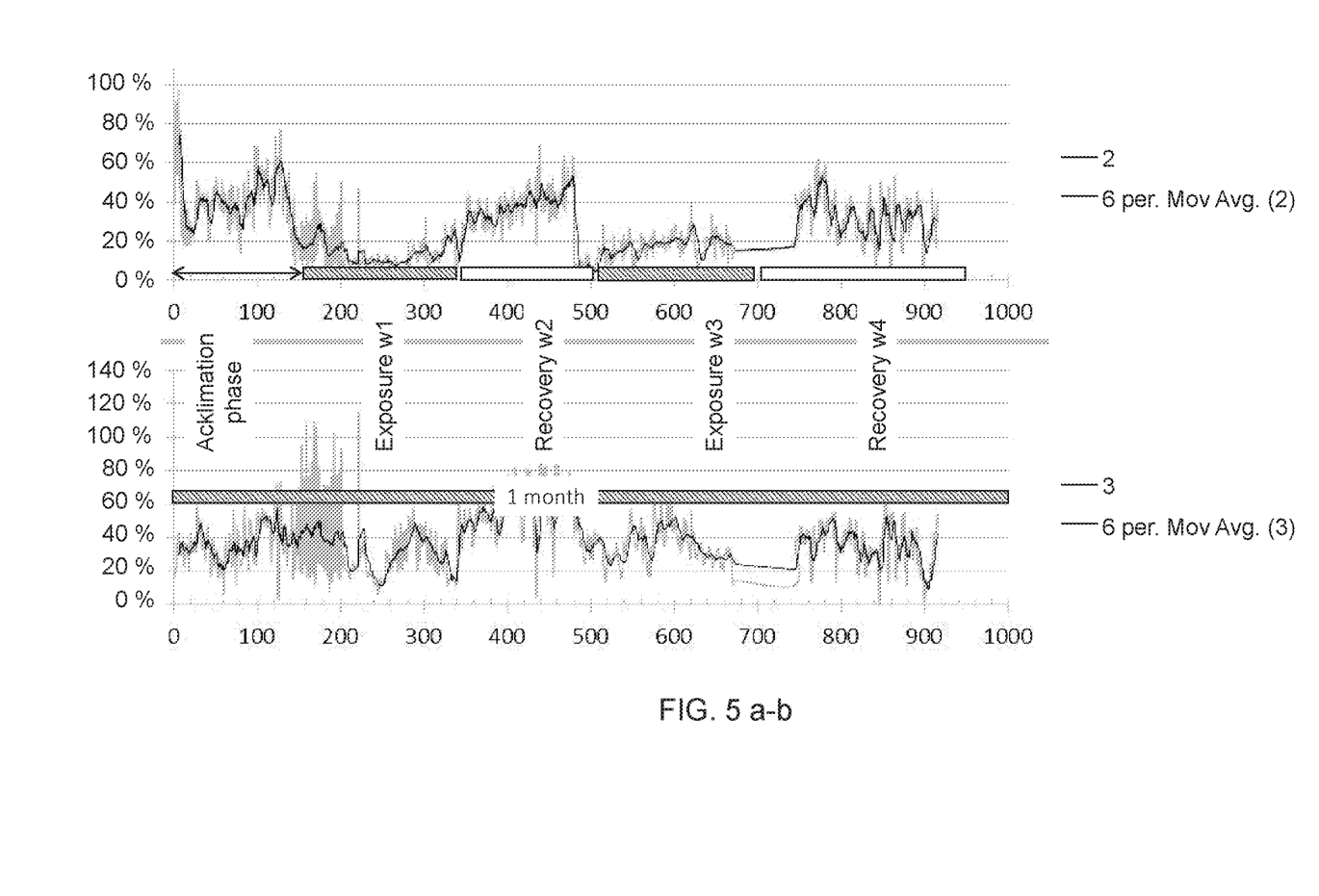
FIG. 5a-b show time-lapse-video-on/off laboratory experiment during 1 month.

Typically, according to an embodiment, for each picture, the coral silhouette CS is measured after pre-processing of the picture in the processing unit 19. This can be analysed by plotting "polyp activity" i. e. coral silhouette changes as measured in pixels, over time and assess a deviance to normal base line activity. In FIG. 5 is shown a rapid response of polyp activity following DC exposure. As shown a gradual recovery post-exposure will be negatively following sedimentation. Exposure w3 following sedimentation shows that the corals have been negatively influenced and will not recover w4 as good as before since the recovery has decreased, i. e. recover w4 is lower than recover w2.

The embodiments of the disclosure system will be particularly useful to document no harmful effect on coral during the whole life cycle of a production field. Particularly the embodiments will be useful to monitor effects on corals during exploration drilling and production, to comply with existing regulation requiring documentation, to minimize the impact of drilling activities and protect environmentally sensitive habitats at the seafloor.

LIST OF REFERENCES

1. Gass, S. E. (2006) The Environmental Sensitivity of Cold-water Corals: Lophelia pertusa. A thesis submitted to the Open University in fulfillment of the requirements of the Degree of Doctor of Philosophy.
2. Larsson, A. I., van Oevelen, D., Purser, A. and Thomsen, L. (2013) Tolerance to longterm exposure of suspended benthic sediments and drill cuttings in the cold-water coral Lophelia pertusa. Marine Pollution Bulletin 70(1-2), 176-188.
3. Roberts, J. M. and Anderson, R. M. (2002) A new laboratory method for monitoring deep-water coral polyp behaviour. Hydrobiologia 471, 143-148.
4. NFR "Havet & kysten" 184699/S40—"Impact of water-based drilling mud in the Barents Sea: a study using the epibenthic coral species Lophelia pertusa"
5. "Workshop on cold-water coral ecosystems: knowledge status, gaps, research needs, and strategy related to O&G operations" Contracted by The Norwegian Oil Industry Association (OLF) http://www.his.no/coralworkshop2010
6.—NFR "Havet & kysten" 204025—"Insights into the sensitivity of cold-water communities to drilling mud: enhancing diagnosis and decision-making with emphasis on Lophelia."

The invention claimed is:

1. A biosensor system for in situ monitoring of deep-water sea-floor biological patterns, comprising a plurality of biosensor devices that are spaced apart proximate a deep-water sea-floor, each biosensor device including:
   a platform and
   a plurality of cameras and a lighting system mounted on the platform,
   wherein the cameras define respective picture frames,
   wherein a plurality of coral nubbins with a plurality of polyps are prepared and fixed to a platform of the biosensor platform with a distance to each other such that there is no overlap in respective picture frames of the cameras,
   wherein the cameras and the lighting system are arranged on the platform in relation to the plurality of coral nubbins in order to take coral-silhouette-pictures of the plurality of nubbins in respective picture frames, and
   an analyser for analysing changes in the coral-silhouette-pictures taken over time, and wherein the analyser causes an alarm to be given as a function of a threshold value.
2. The biosensor system according to claim 1, wherein the coral nubbins comprise 4 to 8 polyps.
3. The biosensor system according to claim 2, wherein the coral nubbins have tree-like structure.
4. The biosensor system according to claim 1, further comprising a picture processing and communication unit arranged to communicate data for in situ pre-processing and measuring coral silhouettes of each coral nubbin in an analytical unit for processing coral data including at least the coral silhouette.
5. The biosensor system according to claim 1, wherein the lighting system and the cameras are adapted to be turned on during a period of time of 1 to 5 minutes so as to reduce power consumption and coral light-exposure.
6. The biosensor system according to claim 1, wherein the plurality of biosensor devices are spaced apart at a distance of 300 to 500 meters on the deep-water sea-floor.

7. The biosensor system according to claim 1, wherein the analyser processes coral data received from or transmitted to the biosensor devices.

8. The biosensor system according to claim 7, wherein the analyser is arranged to give each coral nubbin a unique identification, and the coral: silhouette: pictures and associated coral silhouette areas are arranged to be recorded automatically with shooting time.

9. The biosensor system, according to claim 8, further comprising a communications unit adapted to transmit coral data, including at least measured coral silhouette data, to an operational centre that can communicate with the biosensor system.

10. A method for monitoring deep-water sea-floor biological patterns with a biosensor system comprising a plurality of biosensor devices that are spaced apart proximate a deep-water sea-floor, each biosensor device including a platform and a plurality of cameras and a lighting system mounted on the platform, wherein a plurality of coral nubbins with a plurality of polyps are prepared and fixed to the platform of the biosensor device with a distance to each other such that there is no overlap in respective picture frames of the cameras, and wherein the cameras and the lighting system are arranged on the platform in relation to the plurality of coral nubbins in order to take coral-silhouette-pictures of the plurality of nubbins in respective picture frames, the method comprising using the biosensor system to take coral-silhouette-pictures over time; followed by using an analyser to analyse changes in the coral-silhouette-pictures taken over time, and causing an alarm to be given as a function of a threshold value.

11. The method according to claim 10, wherein the coral nubbins are collected from a clean site and acclimatized under field conditions.

12. The method according to claim 10, wherein the lighting system and the cameras are turned on during a period of time of 1 to 5 minutes so as to reduce power consumption and coral light-exposure.

13. The method according to claim 10, wherein each coral nubbin is given a unique identification by the analyser, and the coral-silhouette-pictures and corresponding coral silhouette areas are recorded automatically with shooting time.

14. The method according to claim 10, wherein the function of the threshold value includes deviating from baseline values or for too small coral silhouette area is passed.

* * * * *